(12) United States Patent
Tsao et al.

(10) Patent No.: US 7,198,421 B2
(45) Date of Patent: Apr. 3, 2007

(54) ENCLOSED OPENING MEANS

(75) Inventors: Tawei Tsao, Diamond Bar, CA (US);
Shun-I Pan, San Gabriel, CA (US);
Garry Tsaur, 19222 Tranbarger St.,
Rowland Heights, CA (US) 91748

(73) Assignee: Garry Tsaur, Rowland Heights, CA (US)

( * ) Notice: Subject to any disclaimer, the term of this patent is extended or adjusted under 35 U.S.C. 154(b) by 0 days.

(21) Appl. No.: 10/728,701

(22) Filed: Dec. 5, 2003

(65) Prior Publication Data

US 2005/0123339 A1 Jun. 9, 2005

(51) Int. Cl.
*B43K 5/14* (2006.01)
*B43K 5/00* (2006.01)
*A61M 35/00* (2006.01)

(52) U.S. Cl. .................. 401/133; 401/132; 401/205; 604/3

(58) Field of Classification Search ........ 401/132–135, 401/205; 222/541.1, 541.3, 541.4, 541.6; 604/3
See application file for complete search history.

(56) References Cited

U.S. PATENT DOCUMENTS

| 3,442,424 | A | * | 5/1969 | Prussin et al. | ................. | 222/81 |
| 3,764,796 | A | * | 10/1973 | Gilliam et al. | ................. | 262/34 |
| 5,658,084 | A | * | 8/1997 | Wirt | ............................. | 401/132 |
| 5,791,801 | A | * | 8/1998 | Miller | ........................ | 401/132 |

* cited by examiner

*Primary Examiner*—David J. Walczak
(74) *Attorney, Agent, or Firm*—Joe Nieh

(57) ABSTRACT

An elongated sealed container with a self-contained opening means fully enclosed within the container to release a fluid sealed within the container when the container is bent at or near the enclosed opening means. Once the enclosed opening means is opened, the fluid sealed within the elongated sealed container may be released for application.

21 Claims, 3 Drawing Sheets

ENCLOSED OPENING MEANS

BACKGROUND-FIELD OF INVENTION

The present invention relates generally to a sealed container with an opening means enclosed within the container for releasing a liquid enclosed within the container.

BACKGROUND-DESCRIPTION OF RELATED ART

A variety of opening means exists for opening a container. Most opening means are in the form of a screw-on cap or a snap-on cap. Some opening means are in the form of a frangible seal or a score line on the container that will allow the contents of the container to be released upon fracturing of the frangible seal or the container at the score line. All of these opening means are either attached to the container externally, such as the screw-on cap and the snap-on cap, or are formed as part of the container, such as the frangible seal and the score line on the container. None of the opening means are designed to be enclosed within the container to seal a liquid in the container and yet still allow the release of the liquids easily and reliably. The availability of an effective and easy to use opening means is particularly lacking for a small elongated container with a small cross-sectional area.

In applicant's pending U.S. patent application, U.S. patent application Ser. No. 10/670,961, applicant disclosed numerous enclosed opening means that are designed to be enclosed within the container to seal a liquid in the container and to allow the release of the liquid easily and reliably. One of the design for the enclosed opening means comprises of a cylinder with an outside diameter approximately that of the inside diameter of an elongated tubular housing defining a small liquid flow path from the open end of the elongated tubular housing to the liquid. The end near the liquid has an elongated protrusion that is smaller in diameter than the cylindrical body of the enclosed opening means and is separable from the cylindrical body of the enclosed opening means. The elongated protrusion seals the small liquid flow path in the cylinder and prevents the liquid in the elongated tubular housing from being released through the enclosed opening means. When the elongated tubular housing is bent near the junction between the elongated protrusion and the cylindrical body of the enclosed opening means, the elongated protrusion will be separated from the cylindrical body and the small liquid path is exposed for the liquid to be released from the elongated tubular housing through the opening means.

This particular design has several drawbacks. When the elongated tubular housing is squeezed to force the liquid out of the elongated tubular housing, the elongated protrusion will interfere with the compression of the elongated tubular housing since it is disposed within the liquid where it is being squeezed. This will result in less effective extraction of the liquid since the elongated protrusion will limit the amount of squeezing that can be applied to the liquid. Furthermore, since the elongated protrusion remains within the liquid after being severed, the elongated protrusion may interfere with the liquid flow path when the liquid is being forced out of the elongated tubular housing. The severed elongated protrusion may flow with the liquid and plug the opening thereby restricting or completely cut-off the liquid flow.

SUMMARY OF THE INVENTION

The present invention is an elongated sealed container with a self-contained opening means fully enclosed within the container to release the fluid sealed within the container. The enclosed opening means is operated by bending the elongated sealed container at or near the enclosed opening means. Once the enclosed opening means is opened, the fluid sealed within the elongated sealed container may be released for application. The present invention will not interfere with the squeezing of the elongated sealed container or the fluid flow. When the elongated sealed container has a small cross-section such that the fluid within it cannot be released due to its surface tension, a guiding member may be utilized to increase the capillary action and to overcome the surface tension of the fluid to release the fluid from the elongated sealed container.

DETAILED DESCRIPTION OF THE PREFERRED EMBODIMENT

Figure 1:
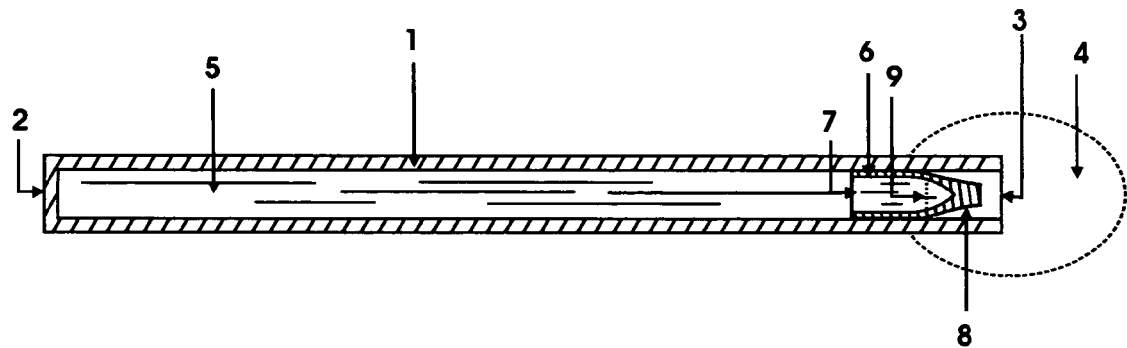
FIG. 1 shows a cross-sectional view of the preferred embodiment of the enclosed opening means.
Figure 2:
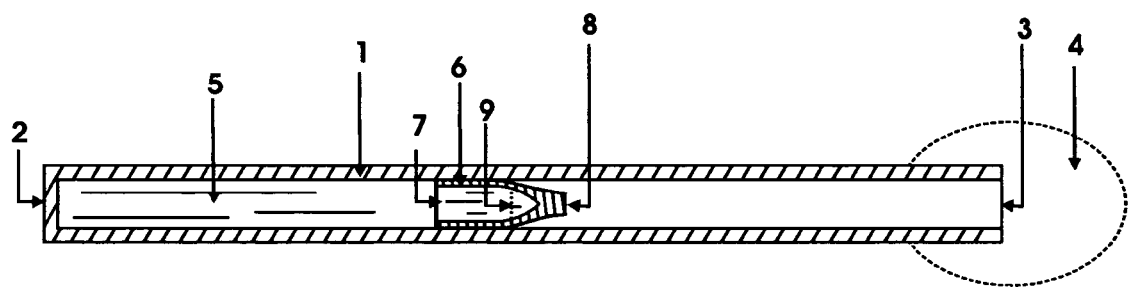
FIG. 2 shows a cross-sectional view of another embodiment of the enclosed opening means.

FIGS. 1 and 2 show the preferred embodiment of the enclosed opening means. In the preferred embodiment, the enclosed opening means is used in an elongated tubular housing 1 with a sealed end 2 and an open end 3. An applicator tip 4 such as a cotton swab, a foam tip, or a brush may be affixed to the open end 3 of the elongated tubular housing 1. A fluid 5 is enclosed within the elongated tubular housing 1 near the sealed end 2. An enclosed opening means 6 is disposed inside the elongated tubular housing 1 sealing the fluid 5 within the elongated tubular housing 1. The opening means 6 is operated by bending the elongated tubular housing 1 at or near the enclosed opening means 6. The opening means 6 may be disposed at any location within the elongated tubular housing 1. As shown in FIG. 1, the opening means 6 may be positioned near the open end 3 of the elongated tubular housing 1 to allow the maximum amount of fluid 5 and to allow bending of the elongated tubular housing 1 by pressing the open end 3 on a surface to open the opening means 6. As shown in FIG. 2, the opening means 6 may also be positioned away from the open end 3 of the elongated tubular housing 1 thereby the bending of the elongated tubular housing 1 may be accomplished without contact with the open end 3 of the elongated tubular housing 1 if an applicator tip 4 such as a cotton swab is affixed to the open end 3.

The enclosed opening means 6 comprises of a cylinder with an open end 7 and a sealed end 8. A sealing diameter is provided around the cylinder that is approximately that of the inside diameter of the elongated tubular housing 1 and provides a seal to prevent the release of the fluid 5 from between the elongated tubular housing 1 and the opening means 6. The outside diameter at the sealed end 8 is smaller than the inside diameter of the elongated tubular housing 1. A fracture line 9 is provided near the sealed end 8 of the cylinder at a location on the other side of the sealing diameter where the fluid 5 is disposed. The enclosed opening means 6 is inserted into the elongated tubular housing 1 with its open end 7 towards the fluid 5 thereby sealing the fluid 5 within the elongated tubular housing 1. When the elongated tubular housing 1 is bent at or near the fracture line 9 on the cylinder, the cylinder will be separated into two sections thereby exposing a small fluid path from the fluid 5 through the enclosed opening means 6 to the open end 3 of the elongated tubular housing 1 for the fluid 5 to be released from the elongated tubular housing 1 through the opening means 6.

Figure 3:
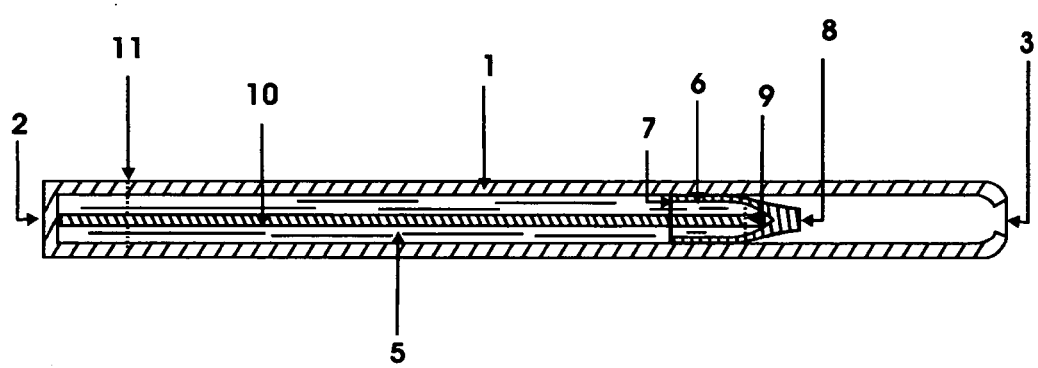
FIG. 3 shows a cross-sectional view of another embodiment of the enclosed opening means.

As shown in FIG. 3, the elongated tubular housing 1 may be provided with a reduced opening at its open end 3 to capture the fractured sealed end 8 of the enclosed opening means 6 if an applicator tip is not provided. The reduced opening is provided with a profile that will maintain a fluid flow path even if the fractured sealed end 8 of the enclosed opening means 6 is lodged against it. This may be accomplished by forming the reduced opening in an elliptical shape or in any other shape that is different than the shape of the fractured sealed end 8 of the enclosed opening means 6.

When the elongated tubular housing 1 has a small cross-section such that the fluid 5 within it cannot be reliably released simply by opening the opening means 6 due to its surface tension, a guiding member 10 may be utilized to increase the capillary action and to overcome the surface tension of the fluid 5 to release the fluid 5 from the elongated tubular housing 1 as shown in FIG. 3. The guiding member 10 may be affixed to the sealed end 2 of the elongated tubular housing 1 and extends to near or slightly inside the open end 7 of the opening means 6.

If the guiding member 10 is affixed to the sealed end 2 of the elongated tubular housing 1 and with its free end formed as a pointed end, it may be used as a toothpick after the fluid 5 is depleted. A fracture line 11 is provided near the sealed end 2 of the elongated tubular housing 1 to allow separating the sealed end 2 with the guiding member/toothpick 10 from the remainder of the elongated tubular housing 1 and to expose the pointed end of the guiding member/toothpick 10 for use as a toothpick.

Figure 4:
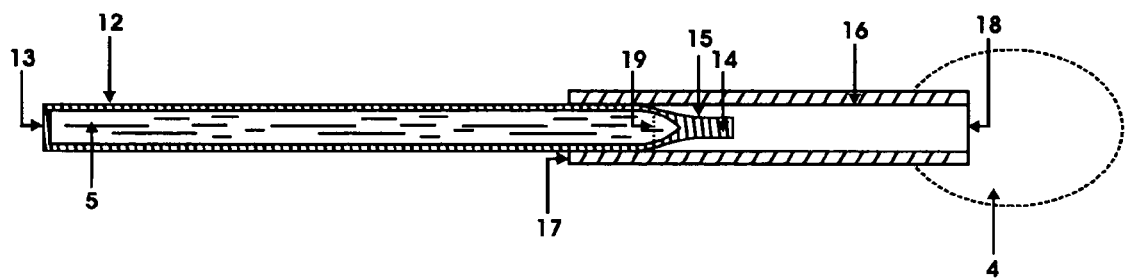
FIG. 4 shows a cross-sectional view of another embodiment of the enclosed opening means.

FIG. 4 shows another embodiment of the enclosed opening means. In this embodiment, the enclosed opening means 15 is formed as a sealed end 14 of an elongated tubular housing 12 with two sealed ends 13, 14 enclosing a fluid 5. The end 14 of the elongated tubular housing 12 with the enclosed opening means 15 is inserted into a second tubular housing 16 with two open ends 17, 18. One open end 17 of the second tubular housing 16 seals around the end 14 of the elongated tubular housing 12 with the enclosed opening means 15 at a location past the fracture line 19. An applicator tip 4 such as a cotton swab, a foam tip, or a brush may be affixed to the other open end 18 of the second tubular housing 16.

Figure 5:
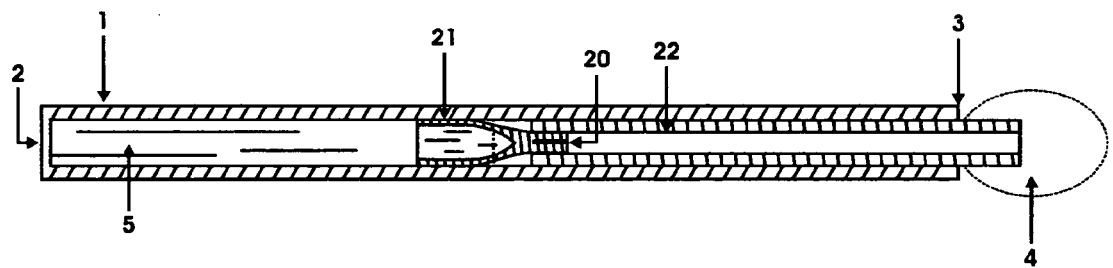
FIG. 5 shows a cross-sectional view of another embodiment of the enclosed opening means.

FIG. 5 shows another embodiment of the enclosed opening means. In this embodiment, the sealed end 20 of the enclosed opening means 21 has a circumference that provides one or more fluid flow path around the sealed end 20. The sealed end 20 may be formed in the shape of a geometric shape that is not a circle such as a triangle, a square, or a star shape such that when it is inserted into another tube 22 it will not seal off the tube 22 but would leave one or more fluid flow path between the sealed end 20 and the tube 22. The enclosed opening means 21 is used in an elongated tubular housing 1 with a sealed end 2 and an open end 3. A fluid 5 is enclosed within the elongated tubular housing 1 near the sealed end 2. The enclosed opening means 21 is disposed inside the elongated tubular housing 1 sealing the fluid 5 within the elongated tubular housing 1. Another tube 22 with two open ends is inserted into the open end 3 of the elongated tubular housing 1 with one open end toward the sealed end 20 of the enclosed opening means 21 overlapping the sealed end 20 of the enclosed opening means 21 and the other open end protruding from the open end 3 of the elongated tubular housing 1. An applicator tip 4 such as a cotton swab, a foam tip, or a brush may be affixed to the protruding open end of the tube 22.

Figure 6:
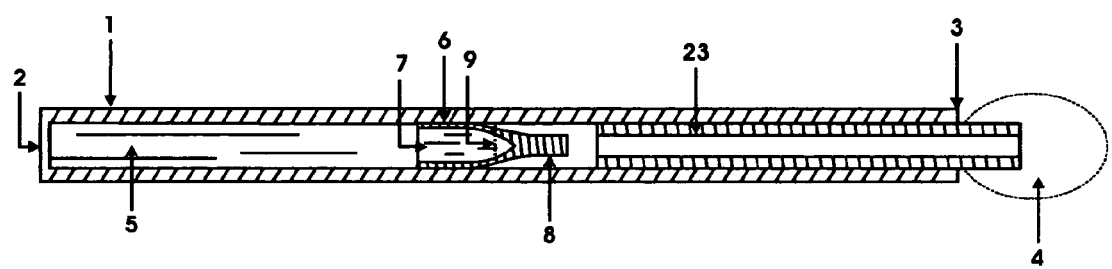
FIG. 6 shows a cross-sectional view of another embodiment of the enclosed opening means.

FIG. 6 shows another embodiment of the enclosed opening means. In this embodiment, the enclosed opening means 6 is used in an elongated tubular housing 1 with a sealed end 2 and an open end 3. A fluid 5 is enclosed within the elongated tubular housing 1 near the sealed end 2. An enclosed opening means 6 is disposed inside the elongated tubular housing 1 sealing the fluid 5 within the elongated tubular housing 1. Another tube 23 with two open ends is inserted into the open end 3 of the elongated tubular housing 1 with one open end disposed toward the sealed end 8 of the enclosed opening means 6 and the other open end protruding from the open end 3 of the elongated tubular housing 1. An applicator tip 4 such as a cotton swab, a foam tip, or a brush may be affixed to the protruding open end of the tube 23.

Figure 7:
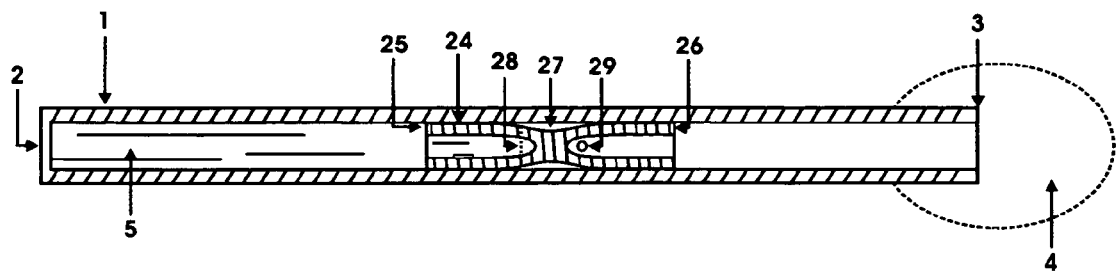
FIG. 7 shows a cross-sectional view of another embodiment of the enclosed opening means.

FIG. 7 shows another embodiment of the enclosed opening means comprising a tubular section 24 with two open ends 25, 26 and a seal 27 separating the two open ends 25, 26 disposed within the tubular section 24 between the two open ends 25, 26. In the preferred embodiment, the enclosed opening means is affixed in the elongated tubular housing. The outside diameter of the tubular section 24 near the seal 27 is smaller than the outside diameter of the tubular section 24 near the two open ends 25, 26. A fracture line 28 is formed on one side of the seal 27 disposed at the section with the reduced outside diameter. An opening 29 such as a hole is formed on the other side of the seal 27 disposed at the section with the reduced outside diameter. The enclosed opening means 24 is inserted into an elongated tubular housing 1 with a sealed end 2 and an open end 3 enclosing a fluid 5 disposed near the sealed end 2. In the preferred embodiment, the enclosed opening means 24 is inserted such that the open end 25 with the fracture line 28 is disposed towards the fluid 5 and the open end 26 with the opening 29 is disposed toward the open end 3 of the elongated tubular housing 1. An applicator tip 4 such as a cotton swab, a foam tip, or a brush may be affixed to the open end 3 of the elongated tubular housing 1. When the elongated tubular housing 1 is bent at or near the fracture line 28 on the enclosed opening means 24 a fluid flow path is exposed leading from the fluid 5 to the open end 3 of the elongated tubular housing 1. The fluid 5 will flow through the resulting opening from the fracture of the fracture line 28 into the area between the reduced outside diameter of the enclosed opening means 24 and the inside wall of the elongated tubular housing 1 and then into the opening 29 on the other side of the seal 27 in the enclosed opening means 24 and out of the elongated tubular housing 1.

Figure 8:
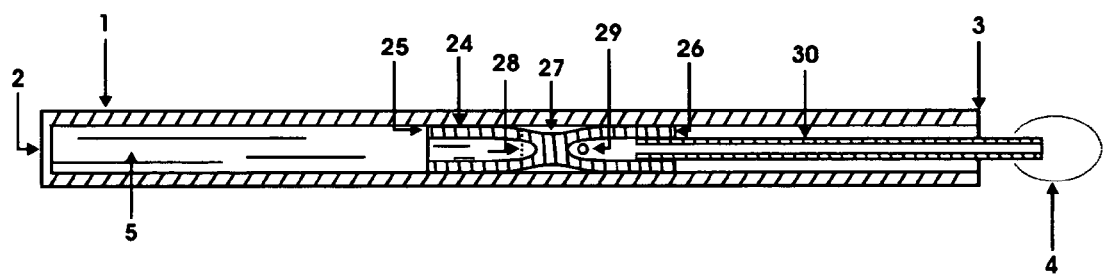
FIG. 8 shows a cross-sectional view of another embodiment of the enclosed opening means.

FIG. 8 shows another embodiment of the enclosed opening means wherein a hollow tube 30 is inserted through the open end 3 of the elongated tubular housing 1 and into the open end 26 of the enclosed opening means 24 shown in FIG. 7. An applicator tip 4 such as a cotton swab, a foam tip, or a brush may be affixed to the open end of the hollow tube 30 that is exposed outside of the elongated tubular housing 1. In this embodiment, a more rigid hollow tube 30 may be used to increase the rigidity of the body of the elongated tubular housing 1 near the applicator tip 4.

Figure 9:
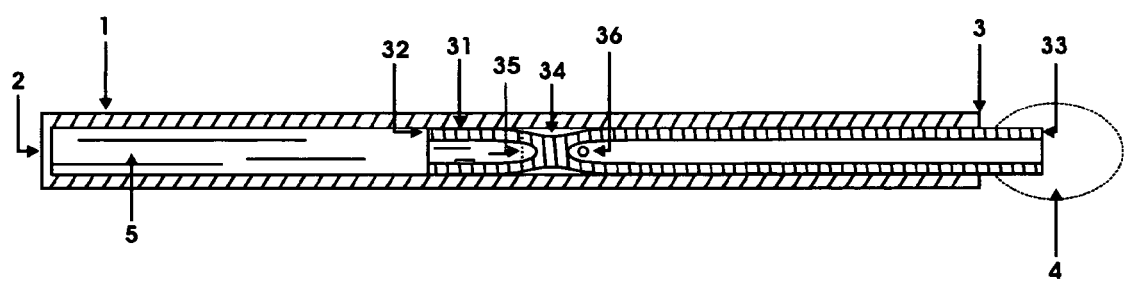
FIG. 9 shows a cross-sectional view of another embodiment of the enclosed opening means.

FIG. 9 shows another embodiment of the enclosed opening means previously shown in FIG. 7 comprising a tubular section 31 with two open ends 32, 33 and a seal 34 separating the two open ends 32, 33 disposed within the tubular section 31 between the two open ends 32, 33. The outside diameter of the tubular section 31 near the seal 34 is smaller than the outside diameter of the tubular section 31 near the two open ends 32, 33. A fracture line 35 is formed on one side of the seal 34 disposed at the section with the reduced outside diameter. An opening 36 such as a hole is formed on the other side of the seal 34 disposed at the section with the reduced outside diameter. The enclosed opening means 31 is inserted into an elongated tubular housing 1 with a sealed end 2 and an open end 3 enclosing a fluid 5 disposed near the sealed end 2. The enclosed opening means 31 is inserted such that the open end 32 with the fracture line 35 is disposed towards the fluid 5 and the open end 33 with the opening 36 is disposed toward the open end 3 of the elongated tubular housing 1 wherein the open end 33 of the enclosed opening means 31 extends out of the elongated tubular housing 1. An applicator tip 4 such as a cotton swab, a foam tip, or a brush may be affixed to the open end 33 of the enclosed opening means 31. When the elongated tubular housing 1 is bent at or near the fracture line 35 on the enclosed opening means 31 a fluid flow path is exposed leading from the fluid 5 to the open end 33 of the enclosed opening means 31. The fluid 5 will flow through the resulting opening from the fracture of the fracture line 35 into the area between the reduced outside diameter of the enclosed opening means 31 and the inside wall of the elongated tubular housing 1 and then into the opening 36 on the other side of the seal 34 in the enclosed opening means 31 and out of the elongated tubular housing 3.

Although the description above contains many specificities, these should not be construed as limiting the scope of the invention but as merely providing illustrations of some of the presently preferred embodiments of this invention. Thus the scope of the invention should be determined by the appended claims and their legal equivalents, rather than by the examples given.

What is claimed is:

1. An enclosed opening means comprising:
   an elongated tubular housing with a sealed end and an open end with a fluid disposed near said sealed end; and
   a cylinder with an open end and a sealed end with a sealing diameter provided around said cylinder that is approximately that of the inside diameter of the elongated tubular housing and provides a seal to prevent the release of the fluid from between the elongated tubular housing and the opening means and with an outside diameter at the sealed end of the cylinder smaller than the inside diameter of the elongated tubular housing and a fracture line provided near the sealed end of the cylinder at a location on the other side of the sealing diameter where the fluid is disposed;
   wherein said enclosed opening means is disposed in the elongated tubular housing with the open end towards the fluid thereby sealing the fluid within the elongated tubular housing and whereby said enclosed opening means is operated by bending the elongated tubular housing near the enclosed opening means.

2. An enclosed opening means as in claim 1, wherein an applicator tip is affixed to said open end of said elongated tubular housing.

3. An enclosed opening means as in claim 1 or 2, wherein said open end of said elongated tubular housing has a smaller inside diameter than the elongated tubular housing.

4. An enclosed opening means as in claim 1 or 2, wherein an elongated member is disposed near the sealed end of said elongated tubular housing.

5. An enclosed opening means as in claim 4, wherein said elongated member comprises of a pointed free end and a fixed end affixed to the sealed end of said elongated tubular housing with a fracture line provided near the sealed end of said elongated tubular housing.

6. An enclosed opening means as in claim 1, wherein a tube with two open ends is inserted through the open end of said elongated tubular housing with one open end protruding from said open end of said elongated tubular housing.

7. An enclosed opening means as in claim 6, wherein an applicator tip is affixed to said open end of said tube.

8. An enclosed opening means as in claim 6 or 7, wherein an elongated member is disposed near the sealed end of said elongated tubular housing.

9. An enclosed opening means as in claim 8, wherein said elongated member comprises of a pointed free end and a fixed end affixed to the sealed end of said elongated tubular housing with a fracture line provided near the sealed end of said elongated tubular housing.

10. An enclosed opening means comprising:
    a tubular housing with a first sealed end and a second sealed end with a reduced outside diameter at the second sealed end enclosing a fluid and a fracture line provided near said second sealed end; and
    a tube with generally constant diameter throughout its length and with a first open end and a second open end whereby said first open end encloses the second sealed end of said tubular housing such that it forms a seal around the second sealed end at a location aft of the fracture line;
    wherein when the tube is bent at or near said fracture line, the fluid will be released through the tube.

11. An enclosed opening means as in claim 10, wherein an applicator tip is affixed to said second open end of said tube.

12. An enclosed opening means as in claim 10 or 11, wherein an elongated member is disposed in said tubular housing.

13. An enclosed opening means as in claim 12, wherein said elongated member comprises of a pointed free end and a fixed end affixed to the first sealed end of said tubular housing with a fracture line provided near the first sealed end of said tubular housing.

14. An enclosed opening means comprising:
    an elongated tubular housing with a sealed end and an open end with a fluid disposed near said sealed end; and
    a tubular section with two open ends and a seal separating the two open ends disposed within the tubular section between the two open ends and an outside diameter of the tubular section near the seal that is smaller than an outside diameter of the tubular section near said two open ends with a fracture line provided on one side of the seal disposed at the section with the reduced outside diameter and an opening positioned on the other side of the seal disposed at the section with the reduced outside diameter;

wherein the enclosed opening means is affixed in the elongated tubular housing such that the open end with the fracture line is disposed towards the fluid and the open end with the opening is disposed toward the open end of the elongated tubular housing.

15. An enclosed opening means as in claim 14, wherein an applicator tip is affixed to said open end of said elongated tubular housing.

16. An enclosed opening means as in claim 14 or 15, wherein an elongated member is disposed near the sealed end of said elongated tubular housing.

17. An enclosed opening means as in claim 16, wherein said elongated member comprises of a pointed free end and a fixed end affixed to the sealed end of said elongated tubular housing with a fracture line provided near the sealed end of said elongated tubular housing.

18. An enclosed opening means as in claim 14, wherein a tube with two open ends is inserted through the open end of said elongated tubular housing with one open end protruding from said open end of said elongated tubular housing.

19. An enclosed opening means as in claim 18, wherein an applicator tip is affixed to said open end of said tube that protrudes from said open end of said elongated tubular housing.

20. An enclosed opening means as in claim 18 or 19, wherein an elongated member is disposed near the sealed end of said elongated tubular housing.

21. An enclosed opening means as in claim 20, wherein said elongated member comprises of a pointed free end and a fixed end affixed to the sealed end of said elongated tubular housing with a fracture line provided near the sealed end of said elongated tubular housing.

* * * * *